US 7,794,441 B2

(12) United States Patent
Ashton et al.

(10) Patent No.: US 7,794,441 B2
(45) Date of Patent: Sep. 14, 2010

(54) DUAL CUFF FOR A UNITARY DISPOSABLE ABSORBENT ARTICLE BEING SPACED AWAY FROM BACKSHEET

(75) Inventors: Gregory Ashton, Cincinnati, OH (US); Eiro Fukuda, Mason, OH (US); Masaharu Nishikawa, Montgomery, OH (US)

(73) Assignee: the Procter & Gamble Company, Cincinnati, OH (US)

( * ) Notice: Subject to any disclaimer, the term of this patent is extended or adjusted under 35 U.S.C. 154(b) by 1073 days.

(21) Appl. No.: 10/824,121

(22) Filed: Apr. 14, 2004

(65) Prior Publication Data

US 2005/0234410 A1    Oct. 20, 2005

(51) Int. Cl.
*A61F 13/15* (2006.01)
*A61F 13/20* (2006.01)

(52) U.S. Cl. ............... 604/385.28; 604/385.24; 604/385.25; 604/385.27

(58) Field of Classification Search .......... 604/358, 604/385.25, 385.27, 385.28
See application file for complete search history.

(56) References Cited

U.S. PATENT DOCUMENTS

| | | | |
|---|---|---|---|
| 2,075,189 | A | 3/1937 | Galligan et al. |
| 3,025,199 | A | 3/1962 | Harwood |
| 3,848,594 | A | 11/1974 | Buell |
| 3,860,003 | A | 1/1975 | Buell |
| 3,911,173 | A | 10/1975 | Sprague, Jr. |
| 3,920,017 | A | 11/1975 | Karami |
| 3,929,135 | A | 12/1975 | Thompson |
| 4,107,364 | A | 8/1978 | Sisson |
| 4,209,563 | A | 6/1980 | Sisson |
| 4,324,246 | A | 4/1982 | Mullane et al. |
| 4,342,314 | A | 8/1982 | Radel et al. |
| 4,463,045 | A | 7/1984 | Ahr et al. |
| 4,515,595 | A | 5/1985 | Kievit et al. |
| 4,573,986 | A | 3/1986 | Minetola et al. |
| 4,609,518 | A | 9/1986 | Curro et al. |

(Continued)

FOREIGN PATENT DOCUMENTS

EP    0677284 A1    10/1995

(Continued)

OTHER PUBLICATIONS

PCT International Search Report—European Patent Office, Oct. 27, 2005.

*Primary Examiner*—Melanie J Hand
(74) *Attorney, Agent, or Firm*—Charles R. Ware

(57) ABSTRACT

A unitary disposable absorbent article includes: an absorbent core having a garment surface and a body surface, a liquid permeable topsheet positioned adjacent said body surface of said absorbent core, a liquid impermeable backsheet positioned adjacent said garment surface of said absorbent core and an elastically contractible dual cuff. The dual cuff has a proximate end and a distal end. The dual cuff is joined to the article by an intermediate bond. The dual cuff has a first cuff and a second cuff. The first cuff is disposed between the proximate end and the intermediate bond. The second cuff is disposed between the intermediate bond and the distal end. The dual cuff is constructed of a continuous cuff material and enclosed by a cuff end bond. The second cuff is spaced away from the backsheet. The backsheet extends outboard of the distal end.

17 Claims, 3 Drawing Sheets

U.S. PATENT DOCUMENTS

| | | | |
|---|---|---|---|
| 4,610,678 A | 9/1986 | Weisman et al. |
| 4,629,643 A | 12/1986 | Curro et al. |
| 4,657,539 A | 4/1987 | Hasse |
| 4,673,402 A | 6/1987 | Weisman et al. |
| 4,695,278 A | 9/1987 | Lawson |
| 4,699,622 A | 10/1987 | Toussant et al. |
| 4,704,115 A | 11/1987 | Buell |
| 4,704,116 A | 11/1987 | Enloe |
| 4,738,677 A | 4/1988 | Foreman |
| 4,743,246 A | 5/1988 | Lawson |
| 4,785,996 A | 11/1988 | Ziecker et al. |
| 4,795,452 A | 1/1989 | Blaney |
| 4,795,454 A | 1/1989 | Dragoo |
| 4,808,177 A | 2/1989 | Desmarais |
| 4,808,178 A | 2/1989 | Aziz et al. |
| 4,816,025 A | 3/1989 | Foreman |
| 4,822,435 A | 4/1989 | Igaue |
| 4,834,735 A | 5/1989 | Alemany et al. |
| 4,834,741 A | 5/1989 | Sabee |
| 4,842,666 A | 6/1989 | Werenicz |
| 4,846,815 A | 7/1989 | Scripps |
| 4,846,825 A | 7/1989 | Enloe |
| 4,888,231 A | 12/1989 | Angstadt |
| 4,892,528 A | 1/1990 | Suzuki |
| 4,904,251 A | 2/1990 | Igaue |
| 4,909,803 A | 3/1990 | Aziz et al. |
| 4,938,753 A | 7/1990 | Van Gompel et al. |
| 4,938,755 A | 7/1990 | Foreman |
| 4,946,527 A | 8/1990 | Battrell |
| 4,963,140 A | 10/1990 | Robertson et al. |
| 4,988,344 A | 1/1991 | Reising et al. |
| 4,988,345 A | 1/1991 | Reising et al. |
| 5,006,394 A | 4/1991 | Baird |
| 5,019,067 A | 5/1991 | Simmons |
| 5,021,051 A | 6/1991 | Hiuke |
| 5,026,364 A | 6/1991 | Robertson |
| 5,037,416 A | 8/1991 | Allen et al. |
| 5,080,658 A | 1/1992 | Igaue |
| 5,087,255 A | 2/1992 | Sims |
| 5,114,420 A | 5/1992 | Igaue |
| 5,143,679 A | 9/1992 | Weber et al. |
| 5,147,345 A | 9/1992 | Young et al. |
| 5,151,092 A | 9/1992 | Buell et al. |
| 5,156,793 A | 10/1992 | Buell et al. |
| 5,167,653 A | 12/1992 | Igaue |
| 5,167,897 A | 12/1992 | Weber et al. |
| 5,190,563 A | 3/1993 | Herron et al. |
| 5,221,274 A | 6/1993 | Buell et al. |
| 5,224,941 A | 7/1993 | Simmons |
| 5,234,423 A | 8/1993 | Alemany et al. |
| 5,254,111 A | 10/1993 | Cancio |
| 5,260,345 A | 11/1993 | DesMarais et al. |
| 5,269,775 A | 12/1993 | Freeland et al. |
| 5,330,458 A | 7/1994 | Buell et al. |
| 5,342,338 A | 8/1994 | Roe |
| 5,413,570 A | 5/1995 | Enloe |
| 5,454,803 A | 10/1995 | Sageser |
| 5,518,801 A | 5/1996 | Chappell et al. |
| 5,536,350 A | 7/1996 | Klemp |
| 5,542,943 A | 8/1996 | Sageser |
| 5,554,145 A | 9/1996 | Roe et al. |
| 5,569,234 A | 10/1996 | Buell et al. |
| 5,571,096 A | 11/1996 | Dobrin et al. |
| 5,577,540 A | 11/1996 | Sageser |
| 5,580,411 A | 12/1996 | Nease et al. |
| 5,582,606 A | 12/1996 | Bruemmer |
| 5,584,828 A | 12/1996 | Yamamoto |
| H1630 H | 1/1997 | Roe |
| 5,591,152 A | 1/1997 | Buell et al. |
| 5,607,760 A | 3/1997 | Roe |
| 5,609,587 A | 3/1997 | Roe |
| 5,635,191 A | 6/1997 | Roe et al. |
| 5,643,243 A | 7/1997 | Klemp |
| 5,643,588 A | 7/1997 | Roe et al. |
| 5,662,637 A | 9/1997 | Kitaoka |
| 5,669,896 A * | 9/1997 | Kielpikowski ......... 604/385.28 |
| 5,669,897 A | 9/1997 | Lavon et al. |
| 5,672,166 A | 9/1997 | Vandemoortele |
| 5,674,213 A | 10/1997 | Sauer |
| 5,676,661 A | 10/1997 | Faulks |
| 5,769,836 A | 6/1998 | Klemp |
| 5,776,122 A | 7/1998 | Faulks |
| 5,824,172 A | 10/1998 | Kielpikowski |
| 5,827,387 A | 10/1998 | Reynolds |
| 5,851,204 A | 12/1998 | Mizutani |
| 5,865,823 A | 2/1999 | Curro |
| 5,895,382 A | 4/1999 | Popp |
| 5,899,894 A | 5/1999 | Palumbo |
| 5,904,675 A | 5/1999 | Laux |
| 5,911,713 A | 6/1999 | Yamada et al. |
| 5,931,825 A | 8/1999 | Kuen |
| 5,931,826 A | 8/1999 | Faulks |
| 5,938,648 A | 8/1999 | LaVon et al. |
| 5,968,025 A | 10/1999 | Roe et al. |
| 5,993,433 A | 11/1999 | St. Louis |
| 6,004,306 A | 12/1999 | Robles et al. |
| 6,056,733 A | 5/2000 | Kielpikowski |
| 6,102,892 A | 8/2000 | Putzer |
| 6,110,158 A | 8/2000 | Kielpikowski |
| 6,117,121 A | 9/2000 | Faulks |
| 6,120,632 A | 9/2000 | Dragoo |
| 6,121,510 A | 9/2000 | Sauer |
| 6,142,985 A | 11/2000 | Feist |
| 6,156,023 A | 12/2000 | Yoshioka |
| 6,174,302 B1 | 1/2001 | Kumasaka |
| 6,248,097 B1 | 6/2001 | Beitz |
| 6,264,642 B1 | 7/2001 | Kuen |
| 6,293,934 B1 | 9/2001 | Kumasaka |
| 6,328,724 B1 | 12/2001 | Ronnberg |
| 6,346,162 B1 | 2/2002 | Reynolds |
| 6,423,048 B1 | 7/2002 | Suzuki |
| 6,440,117 B1 | 8/2002 | Itoh |
| 6,443,940 B1 | 9/2002 | Ashton et al. |
| 6,450,996 B1 | 9/2002 | Otsubo |
| 6,451,001 B2 | 9/2002 | Kumasaka |
| 6,464,676 B2 | 10/2002 | Mishima |
| 6,506,187 B1 | 1/2003 | Andersson et al. |
| 6,533,765 B1 | 3/2003 | Blaney |
| 6,544,243 B1 | 4/2003 | Inoue |
| 6,547,773 B2 | 4/2003 | Kleinschmidt |
| 6,638,260 B2 | 10/2003 | Mishima |
| 6,641,692 B2 | 11/2003 | Reynolds |
| 6,648,867 B2 | 11/2003 | Minato et al. |
| 6,648,870 B2 | 11/2003 | Itoh |
| 6,716,205 B2 | 4/2004 | Popp et al. |
| 2001/0003153 A1 | 6/2001 | Sayama |
| 2002/0040215 A1 | 4/2002 | Suzuki |
| 2002/0045875 A1 | 4/2002 | Minato |
| 2002/0095129 A1 | 7/2002 | Friderich |
| 2003/0114827 A1 | 6/2003 | Peterson |
| 2003/0208171 A1 | 11/2003 | Zehner |

FOREIGN PATENT DOCUMENTS

| | | |
|---|---|---|
| EP | 0 797 968 A1 | 10/1997 |
| EP | 0978265 A2 | 2/2000 |
| EP | 1 059 072 A2 | 12/2000 |
| EP | 0750894 B1 | 3/2002 |
| EP | 0750895 B1 | 6/2002 |
| EP | 1346713 A2 | 9/2003 |
| JP | 03143443 A | 6/1991 |
| JP | 2874918 B2 | 7/1991 |
| JP | 03-218752 A | 9/1991 |
| JP | 3060466 B2 | 9/1991 |

| | | | | | | | |
|---|---|---|---|---|---|---|---|
| JP | 03218753 | A | 9/1991 | JP | 11318980 | A | 11/1999 |
| JP | 04092665 | A | 3/1992 | JP | 2000042026 | A | 2/2000 |
| JP | 07308341 | A | 11/1995 | JP | 2000079141 | A | 3/2000 |
| JP | 08056984 | A | 3/1996 | JP | 2000140009 | A | 5/2000 |
| JP | 08206154 | A | 8/1996 | JP | 2000271169 | A | 10/2000 |
| JP | 09173370 | A | 7/1997 | JP | 2000300603 | A | 10/2000 |
| JP | 09173380 | A | 7/1997 | JP | 2000300605 | A | 10/2000 |
| JP | 09253126 | A | 9/1997 | JP | 2000-342623 | A | 12/2000 |
| JP | 09276328 | A | 10/1997 | JP | 2001095840 | A | 4/2001 |
| JP | 09276329 | A | 10/1997 | JP | 2001120593 | A | 5/2001 |
| JP | 10075976 | A | 3/1998 | JP | 2001145663 | A | 5/2001 |
| JP | 10113362 | A | 5/1998 | JP | 2001145665 | A | 5/2001 |
| JP | 10192340 | A | 7/1998 | JP | 2002078734 | A | 3/2002 |
| JP | 10-277092 | | 10/1998 | JP | 2003070834 | A | 3/2003 |
| JP | 10277091 | A | 10/1998 | WO | WO 94/05240 | | 3/1994 |
| JP | 1998277092 | A | 10/1998 | WO | WO94/18927 | A1 | 9/1994 |
| JP | 11019121 | A | 1/1999 | WO | WO96/03953 | A1 | 2/1996 |
| JP | 11123207 | A | 5/1999 | WO | WO9605792 | A | 2/1996 |
| JP | 11206807 | A | 8/1999 | WO | WO03/037236 | A2 | 5/2003 |
| JP | 11216163 | A | 8/1999 | WO | WO03/053320 | A1 | 7/2003 |
| JP | 11244326 | A | 9/1999 | | | | |
| JP | 11253490 | A | 9/1999 | | | | |

* cited by examiner

DUAL CUFF FOR A UNITARY DISPOSABLE ABSORBENT ARTICLE BEING SPACED AWAY FROM BACKSHEET

FIELD OF INVENTION

This invention relates to dual cuffs on absorbent articles, and more particularly to dual cuffs having a first cuff and a second cuff on disposable absorbent articles, such as diapers.

BACKGROUND OF THE INVENTION

The major function of absorbent articles, such as disposable diapers and adult incontinent briefs, is to absorb and contain body exudates. Such articles are thus intended to prevent body exudates from soiling, wetting, or otherwise contaminating clothing or other articles, such as bedding, that come in contact with the wearer. One common mode of failure for such products occurs when body exudates leak out of the gaps between the article and the wearer's leg to adjacent clothing because they are not immediately absorbed within the article. For example, urine tends to wick through the topsheet to the edges of the absorbent article where it can come in contact with clothing or other articles. Additionally, loose fecal material that is not easily absorbed by the absorbent article tends to "float" on the liquid-receiving surface and work its way past the legs of the wearer.

Contemporary absorbent articles have a topsheet, a backsheet, an absorbent core, a barrier cuff and a gasketing cuff. The gasketing cuff proves effective generally to prevent wicking and overflow from the fluid laden article to clothing contacting the edges of the article in that the gasketing cuff presents a fluid impermeable barrier between the edge of the article and the contacting clothing, and in addition, provides a gasketing action about the legs of the wearer. The barrier cuff proves effective generally to inhibit loose fecal material or gushes of urine or liquids from soiling the wearer's clothing. The barrier cuff restrains the free flow of this material and provides a structure to hold such material within the article.

Consumers (wearers and/or caregivers) have come to recognize that the cuffs are an important element to the overall effectiveness of the article. As such, the consumer will have more confidence in an article having additional cuffs. However, while cuffs are essential for containment, consumers are also concerned about comfort and minimizing redmarking caused by too much tension in the elastics of the cuffs. Therefore, what is needed is an absorbent article that communicates both effectiveness and comfort in the cuff region.

SUMMARY OF THE INVENTION

A unitary disposable absorbent article includes: an absorbent core having a garment surface and a body surface, a liquid permeable topsheet positioned adjacent said body surface of said absorbent core, a liquid impermeable backsheet positioned adjacent said garment surface of said absorbent core and an elastically contractible dual cuff.

The dual cuff has a proximate end and a distal end. The dual cuff is joined to the article by an intermediate bond. The dual cuff has a first cuff and a second cuff. The first cuff is disposed between the proximate end and the intermediate bond. The second cuff is disposed between the intermediate bond and the distal end. The dual cuff is constructed of a continuous cuff material and enclosed by a cuff end bond. The second cuff is spaced away from the backsheet. The backsheet may extend outboard of the distal end.

The first cuff envelopes at least one elastic which is operatively associated with the first cuff by securing it with an elastic attachment element. The elastic is secured to the first cuff near its ends or along its entire length.

The second cuff envelopes at least one elastic which is operatively associated with the second cuff by securing it with an elastic attachment element. The elastic is secured to the second cuff near its ends or along its entire length.

The absorbent article may be a disposable diaper. The absorbent article may be a prefastened diaper.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

DETAILED DESCRIPTION OF THE INVENTION

Figure 1:
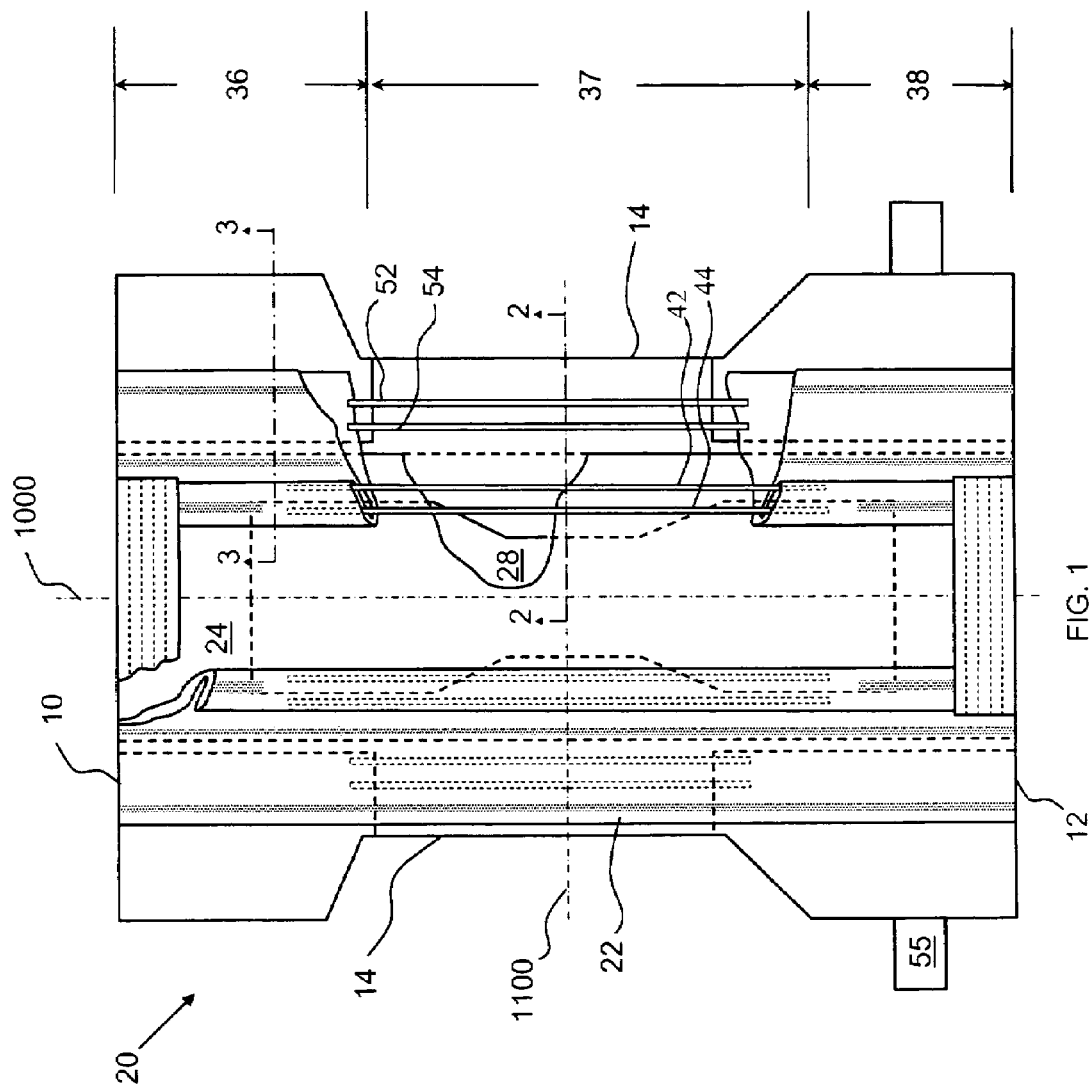
FIG. 1 is a plan view of a disposable diaper embodiment of the present invention having portions cut-away to reveal underlying structure.

As used herein, the following terms have the following meanings:

"Absorbent article" refers to devices that absorb and contain liquid, and more specifically, refers to devices that are placed against or in proximity to the body of the wearer to absorb and contain the various exudates discharged from the body.

"Longitudinal" is a direction running parallel to the maximum linear dimension of the article and includes directions within ±45° of the longitudinal direction.

The "lateral" or "transverse" direction is orthogonal to the longitudinal direction.

The "Z-direction" is orthogonal to both the longitudinal and transverse directions.

The "x-y plane" refers to the plane congruent with the longitudinal and transverse directions.

The term "disposable" is used herein to describe absorbent articles that generally are not intended to be laundered or otherwise restored or reused as an absorbent article (i.e., they are intended to be discarded after a single use and, preferably, to be recycled, composted or otherwise disposed of in an environmentally compatible manner).

As used herein, the term "disposed" is used to mean that an element(s) is formed (joined and positioned) in a particular place or position as a unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "spaced away" encompasses configurations whereby an element is not directly secured to another element.

A "unitary" absorbent article refers to absorbent articles which are formed of separate parts united together to form a coordinated entity so that they do not require separate manipulative parts like a separate holder and liner.

As used herein, the term "diaper" refers to an absorbent article generally worn by infants and incontinent persons about the lower torso.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to pass through its thickness in the absence of a forcing pressure. Conversely, the term "water-impermeable" refers to a layer or a layered structure through the thickness of which liquid water cannot pass in the absence of a forcing pressure. A layer or a layered structure that is water-impermeable according to this definition may be permeable to water vapor, i.e., may be "vapor-permeable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

The terms "proximal" and "distal" refer respectively to the location of an element near to or far from the center of a structure, e.g., the proximal edge of a longitudinally extending element is located nearer to the longitudinal axis than the distal edge of the same element is located relative to the same longitudinal axis.

As used herein, the term "barrier cuff" refers to an elasticized flap which stands substantially upright, more preferably inwardly towards the longitudinal centerline, within the crotch region. Typically, said barrier cuff envelopes/contains at least one elastic that is connected primarily at its opposing ends to the diaper (e.g., drawstring technique for better fit). As used herein, the term "gasketing cuff" refers to an elasticized flap which does not stand substantially upright, more preferably outwardly towards the longitudinal side edges of the diaper, within the crotch region. Typically, said gasketing cuff envelopes/contains at least one elastic that is connected substantially throughout its length to the diaper (e.g., multiple bonds along length of elastic to create gathers).

FIG. 1 is a plan view of an exemplary, non-limiting embodiment of a diaper 20 of the present invention in its flat-out, uncontracted state (i.e., without elastic induced contraction) with portions of the structure being cut away to more clearly show the underlying structure of the diaper 20 and with the portion of the diaper 20 which contacts the wearer facing the viewer. The diaper 20 includes a longitudinal axis 1000 and a lateral axis 1100. One end portion 36 of the diaper 20 is configured as a first waist region 36 of the diaper 20. The opposite end portion 38 is configured as a second waist region 38 of the diaper 20. An intermediate portion 37 of the diaper 20 is configured as a crotch region 37, which extends longitudinally between the first and second waist regions 36 and 38. The waist regions 36 and 38 generally comprise those portions of the diaper 20 which, when worn, encircle the waist of the wearer. The waist regions 36 and 38 may include elastic elements such that they gather about the waist of the wearer to provide improved fit and containment. The crotch region 37 is that portion of the diaper 20 which, when the diaper 20 is worn, is generally positioned between the legs of the wearer. The outer periphery of diaper 20 is defined by longitudinal edges 14 and end edges 10, 12 which are located along the first and second waist region 36, 38, respectively.

The chassis 22 of the diaper 20 comprises the main body of the diaper 20. The chassis 22 comprises an outer covering including a liquid permeable topsheet 24 and/or a liquid impermeable backsheet 26 (see FIG. 2) and at least a portion of an absorbent core 28 encased between the topsheet 24 and the backsheet 26. For unitary absorbent articles, the chassis 22 comprises the main structure of the diaper with other features added to form the composite diaper structure. While the topsheet 24, the backsheet 26, and the absorbent core 28 may be assembled in a variety of well-known configurations, preferred diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method For Manufacturing Side Panels For Absorbent Articles" issued to Nease, et al. on Dec. 3, 1996; and U.S. Pat. No. 6,004,306 entitled "Absorbent Article With Multi-Directional Extensible Side Panels" issued to Robles et al. on Dec. 21, 1999; each of which is incorporated herein by reference.

The topsheet 24 may be fully or partially elasticized or may be foreshortened so as to provide a void space between the topsheet 24 and the core 28. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets"; each of which is incorporated by reference herein.

The absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

Exemplary absorbent structures for use as the absorbent assemblies are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; U.S. Pat. No. 5,397,316 entitled "Slitted Absorbent Members For Aqueous Body Fluids Formed Of Expandable Absorbent Materials" issued to LaVon et al. on Mar. 14, 1995; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997. Each of these patents is incorporated herein by reference.

The backsheet 26 is generally that portion of the diaper 20 positioned adjacent the garment-facing surface of the absorbent core 28. Backsheet 26 prevents the exudates absorbed and contained therein from soiling articles that may contact the diaper 20, such as bed sheets and undergarments. In preferred embodiments, the backsheet 26 is substantially impermeable to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, IN and sold under the trade names X15306, X10962, and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont and copending U.S. patent application Ser. No. 08/744,487, filed on Nov. 6, 1996 in the name of Curro. Other breathable backsheets including nonwoven webs and apertured formed films are described in U.S. Pat. No. 5,571,096 issued to Dobrin et al. on Nov. 5, 1996. An exemplary, suitable backsheet is disclosed in U.S. Pat. No. 6,107,537 entitled "Disposable absorbent articles providing a skin condition benefit" issued to Elder et al on Aug. 22, 2000. Other suitable materials and/or manufacturing techniques may be used to provide a suitable backsheet 26 including, but not limited to, surface treatments, particular film selections and processing, particular filament selections and processing, etc. Each of these references is hereby incorporated by reference herein.

Backsheet 26 may also consist of more than one layer, as exampled in FIG. 1, wherein a backsheet outer layer 26 (often referred to as the backsheet) may be made of a soft, nonwoven material and a backsheet inner layer 27 may be made of a substantially impermeable film. Adhesive 29, or any other suitable material or method, may be used to join layers 26 and 27 together. While a variety of backsheet configurations are contemplated herein, it would be obvious to those skilled in the art that various other changes and modifications can be made without departing from the spirit and scope of the invention.

The diaper 20 may also include a fastening system 55. The fastening system 55 preferably maintains the first waist region 36 and the second waist region 38 in a configuration so as to provide lateral tensions about the circumference of the diaper 20 to hold the diaper 20 on the wearer. The fastening system 55 preferably comprises a surface fastener such as tape tabs, hook and loop fastening components and/or hermaphroditic fastening components, although any other known fastening means are generally acceptable. Some exemplary surface fastening systems are disclosed in U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; the herein before referenced U.S. Pat. No. 5,151,092 issued to Buell on Sep. 9, 1992; and U.S. Pat. No. 5,221,274 issued to Buell on Jun. 22, 1993. An exemplary interlocking fastening system is disclosed in co-pending U.S. application Ser. No. 09/143,184 entitled "Absorbent Article Fastening Device" in the names of Kline et al. filed on Aug. 8, 1998. The fastening system 55 may also provide a means for holding the article in a disposal configuration as disclosed in U.S. Pat. No. 4,963,140 issued to Robertson et al. on Oct. 16, 1990. The fastening system may also include primary and secondary fastening systems, as disclosed in U.S. Pat. No. 4,699,622 entitled "Disposable Diaper Having An Improved Side Closure" issued to Toussant et al. on Oct. 13, 1987. to reduce shifting of overlapped portions or to improve fit as disclosed in U.S. Pat. No. 5,242,436 entitled "Absorbent Article With Fastening System Providing Dynamic Elasticized Waistband Fit" issued to Weil et al. on Sep. 7, 1993; U.S. Pat. No. 5,499,978 entitled "Absorbent Article With Dynamic Elastic Waist Feature Having A Predisposed Resilient Flexural Hinge" issued to Buell et al. on Mar. 19, 1996; U.S. Pat. No. 5,507,736 entitled "Absorbent Article With Dynamic Elastic Waist Feature Comprising An Expansive Tummy Panel" issued to Clear et al. on Apr. 16, 1996; U.S. Pat. No. 5,591,152 entitled "Absorbent Article With Dynamic Elastic Waist Feature Having A Predisposed Resilient Flexural Hinge" issued to Buell et al. on Jan. 7, 1997. Each of these patents and the co-pending application are incorporated herein by reference.

In alternative embodiments, opposing sides of the article may be seamed or welded to form a pant. This allows the article to be used as a pull-on type diaper, such as a training pant. The term "training pants", as used herein, refers to disposable garments having fixed sides and leg openings designed for infant or adults wearers. Training pants (also referred in the art as "pull on" products) are placed in position on the wearer by inserting the wearer's legs into the leg openings and sliding the training pant into position about the wearer's lower torso. Suitable training pants are disclosed in U.S. Pat. No. 5,246,433, issued to Hasse, et al. on Sep. 21, 1993, U.S. Pat. No. 5,569,234, issued to Buell et al. on Oct.

29, 1996, U.S. Pat. No. 6,120,487, issued to Ashton on Sep. 19, 2000, U.S. Pat. No. 6,120,489, issued to Johnson et al. On Sep. 19, 2000, U.S. Pat. No. 4,940,464, issued to Van Gompel et al. on Jul. 10, 1990 and U.S. Pat. No. 5,092,861, issued to Nomura et al. on Mar. 3, 1992, the disclosure of each of which is incorporated herein by reference.

The diaper 20 may also include such other features as are known in the art including cuffs, front and rear ear panels, waist cap features, elastics and the like to provide better fit, containment and aesthetic characteristics. Such additional features are well known in the art and are described in U.S. Pat. No. 3,860,003; and U.S. Pat. No. 5,151,092, which are incorporated by reference herein.

For example, diaper 20 may include barrier cuffs or "stand-up" elasticized flaps, as exampled in U.S. Pat. Nos. 4,808,178 and 4,909,803 issued to Aziz et al. on Feb. 28, 1989 and Mar. 20, 1990, respectively.

Additionally, diaper 20 may include gasketing cuffs or "leg cuff" elasticized side flaps, as exampled in U.S. Pat. No. 3,860,003.

A first and second cuff may both be provided by way of a dual cuff, as exampled in U.S. Pat. Nos. 4,695,278 and 4,795,454 issued to Lawson on Sep. 22, 1987 and to Dragoo on Jan. 3, 1989, respectively.

Figure 2:
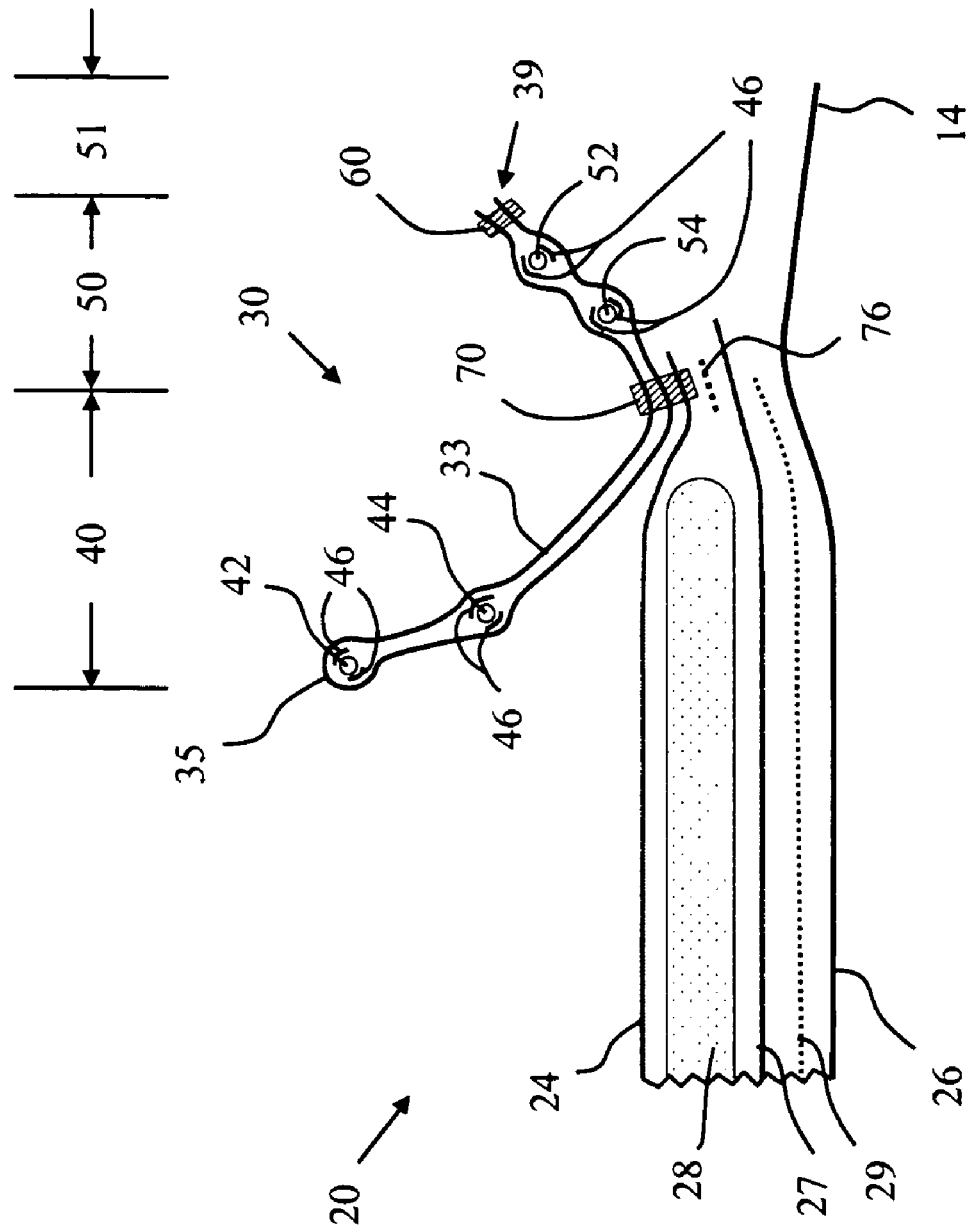
FIG. 2 is a fragmentary sectional view taken along section line 2-2 of FIG. 1.

FIG. 2 is a fragmentary sectional view taken along section line 2-2 of FIG. 1 and depicts the diaper construction in the crotch region 37 of the diaper 20 as it is shaped before being applied to the wearer (i.e., the diaper is subjected to elastic contraction). Dual cuff 30 has a proximate end 35, distal end 39 and regions therebetween identified as first cuff 40 and second cuff 50. Dual cuff 30 may be constructed from a continuous cuff material 33 that substantially envelopes the elastics of first cuff 40 and second cuff 50. More specifically, first cuff 40 has at least one elastic (although two elastics 42, 44 are shown) and second cuff 50 also has at least one elastic (although two elastics 52, 54 are shown) that are enveloped within cuff material 33. In this way, only a continuous cuff material 33 is used and manipulated during the construction of dual cuff 30, thus making easier the manufacturing of said dual cuff. Moreover, cuff material 33 need only be enclosed/bonded at a single location, as exampled by cuff end bond 60, in order to substantially envelope elastics 42, 44, 52, 54, thus providing improved barrier properties by minimizing the number of potential leakable locations (i.e., bonding locations).

Herein, "continuous cuff material" means a cuff material that is continuous along a path beginning from the cuff end bond, along said cuff material, and ending at the same cuff end bond such that the dual cuff 30 is substantially constructed of two layers of the materials, whether it be the same or different materials. For example, the continuous cuff material 33 may be constructed of a lesser-water-permeable material (e.g., spunbound material which is inexpensive) with a more-water-permeable material (e.g., meltblown material which is more expensive) placed inside said lesser-water-permeable material. In another example, cuff material 33 may be constructed of a spunbound-meltblown laminate. In yet another example, cuff material 33 may be constructed of a series of various materials so long as they are continuous. In yet another example, cuff material 33 may be treated to increase its hydrophobicity. Such hydrophobic treatments include, but are not limited to, the application of hydrophobic surface coating (as exampled in co-pending U.S. Patent Application Ser. No. 60/543,785, entitled "Hydrophobic Surface Coated Absorbent Articles And Associated Methods", filed on Feb. 11, 2004) and flouro-treatment (as exampled in co-pending U.S. patent application Ser. No. 10/703,239, entitled "Disposable Absorbent Articles With Masking Topsheet", filed on Nov. 7, 2003). In yet another example, it may be desirable that dual cuff 30 be connected to diaper 20 by way of a single bond (e.g., adhesive, ultrasonic; e.g., intermediate bond 70 to topsheet 24).

Elastics 42, 44, 52, 54 may be operatively associated with their respective cuff by securing it within said cuff with an elastic attachment element 46. The elastic attachment element 46 should be flexible and of sufficient adhesiveness to hold elastics 42, 44, 52, 54 in their stretched condition. Elastics 42, 44, 52, 54, having a first and second end, may be secured to their respective cuff only near their ends or along their entire length. Elastic attachment element 46 may be glue beads made of hot melt adhesive such as marketed by Findley Adhesives Incorporated, Elmgrove, Wis., as Findley Adhesives 581. Alternatively, elastic attachment element 46 may take the form of an ultrasonic bond or heat/pressure seal. A more detailed description of the manner in which the elastic attachment element 46 may be positioned and secured to their respective cuff can be found in U.S. Pat. No. 4,081,301, issued to Buell on Mar. 28, 1978, and in U.S. Pat. No. 4,253,461, issued to Strickland and Visscher on Mar. 3, 1981, both of which are incorporated herein by reference. While elastics 42, 44 in first cuff 40 and elastics 52, 54 in second cuff 50 were shown, it would be obvious to those skilled in the art that one or more elastics may be used in each cuff without departing from the spirit and scope of the invention.

Elastics 42, 44, 52, 54 which have been found suitable are elastic strands having a cross section of 0.18 mm by 1.5 mm and made from natural rubber as available from Easthampton Rubber Company of Stewart, Va., under the trademark L-1900 Rubber Compound. Other suitable elastics can be made from natural rubber, such as elastic tape sold under the trademark Fulflex 9411 by Fulflex Company of Middletown, R. I. Elastics 42, 44, 52, 54 may also comprise any heat shrinkable elastic material as is well known in the art. Other suitable elastic materials may comprise a wide variety of materials as are well known in the art include elastomeric films, polyurethane films, elastomeric foams, formed elastic scrim and synthetic elastomers (e.g., Lycra™). In addition, elastics 42, 44, 52, 54 may take a multitude of configurations. For example, the width may be varied; a single strand or several parallel or non-parallel strands of elastic material may be used; or a variety of shaped may be used including rectilinear and curvilinear.

Dual cuff 30 may be joined to topsheet 24 by way of an intermediate bond 70. Intermediate bond 70 may extend substantially the entire longitudinal length of diaper 20. Intermediate bond 70 may be adhesive, ultrasonic bonding, compression bonding, thermal bonding, combinations thereof, and any other suitable bonding means known in the art which is appropriate for the specific materials employed. Additionally, an adhesive 76 having liquid impermeability properties may be applied between the topsheet 24 and backsheet 26 (or more specifically shown herein, backsheet inner layer 27) to provide improved barrier properties. Adhesive 76 may be located juxtaposed to intermediate bond 70; however, so long as adhesive 76 helps to provide a containment of exudates, then its actual location is may be variable.

As exampled in FIG. 2, second cuff 50 may not be joined to backsheet 26 to provide better conformability of said second cuff to the wearer, thus improving fit and ease of application. Furthermore, it has been discovered that (a) when diaper 20 is worn, (b) when second cuff 50 is spaced away from backsheet 26 and (c) when longitudinal edge 14 of backsheet 26 extends outboard of cuff distal end 39 (as indicated by distance 51), that some consumers believe that an additional barrier layer has been added. And while second cuff 50 already existed, its presence is now more pronounced, thus instilling more product confidence in the consumer. Additionally, it has also been discovered that when longitudinal edge 14 of backsheet 26 extends outboard of cuff distal end 39 of said second cuff 50, said backsheet 26 provides a visual barrier to possible soiling of second cuff 50. Lastly, it has been discovered that some consumers perceive such a product configuration to be softer, more comfortable and even more feminine in appearance which may be especially desirable when marketing disposable diapers to females.

Figure 3:
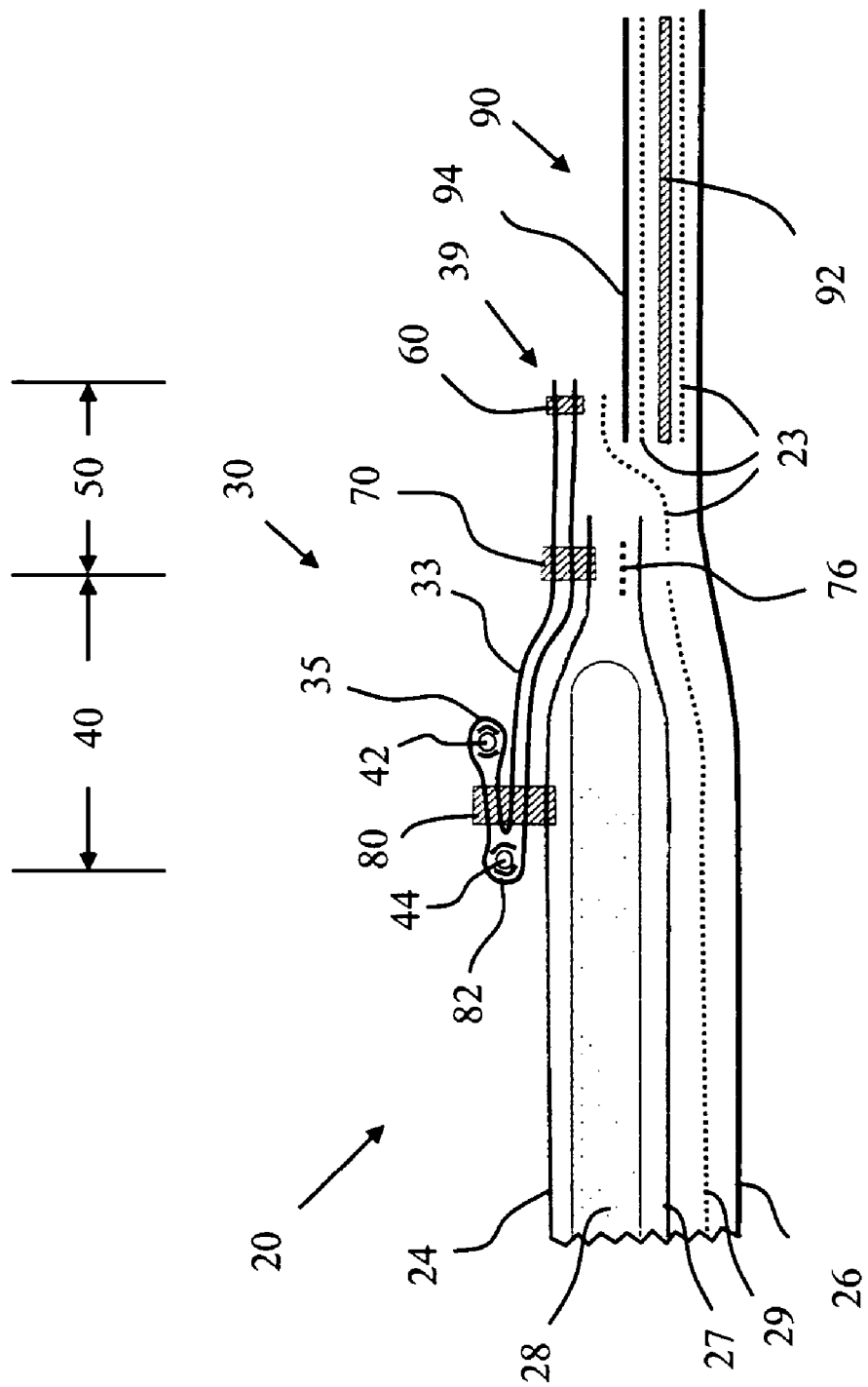
FIG. 3 is a fragmentary sectional view taken along section line 3-3 of FIG. 1.

FIG. 3 is a fragmentary sectional view taken along section line 3-3 of FIG. 1 and depicts the diaper construction in the first waist region 36 of the diaper 20 as it is shaped before being applied to the wearer (i.e., the diaper is subjected to elastic contraction). First cuff 40 is laid down (e.g., folded to create cuff fold 82) and joined to topsheet 24 so as to more readily confirm to the wearer's waist region. First cuff 40 may be joined to topsheet 24 by a cuff tuckdown bond 80 which may be adhesive, ultrasonic bonding, compression bonding, thermal bonding, combinations thereof, and any other suitable bonding means known in the art which is appropriate for the specific materials employed. It some embodiments, it may be desirable for both first cuff 40 and second cuff 50 to be barrier cuffs.

Additionally, side panels 90 may be provided in first and second waist regions 36, 38 and adjacent to longitudinal edges 14. Side panels 90 may comprise a side panel elastic 92 and a side panel cover 94, wherein, the side panel elastic 92 is positioned between said side panel cover 94 and backsheet 26. Adhesive 23, or any other suitable material or method, may be used to join these components together and to cuff distal end 39.

Embodiments of the present invention may also include pockets for receiving and containing waste, spacers which provide voids for waste, barriers for limiting the movement of waste in the article, compartments or voids which accept and contain waste materials deposited in the diaper 20, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al. on Dec. 15, 1992 entitled "Disposable Absorbent Article Having Core Spacers"; U.S. Pat. No. 5,397,318 issued to Dreier on Mar. 14, 1995 entitled "Absorbent Article Having A Pocket Cuff"; U.S. Pat. No. 5,540,671 issued to Dreier on Jul. 30, 1996 entitled "Absorbent Article Having A Pocket Cuff With An Apex"; PCT Application WO 93/25172 published Dec. 3, 1993 entitled "Spacers For Use In Hygienic Absorbent Articles And Disposable Absorbent Articles Having Such Spacer"; U.S. Pat. No. 5,306,266 entitled "Flexible Spacers For Use In Disposable Absorbent Articles" issued to Freeland on Apr. 26, 1994; and U.S. Pat. No. 5,997,520 entitled "Disposable Absorbent Article With Selectively Expandable or Inflatable Component" issued to Ahr et al. on Dec. 7, 1999. Examples of compartments or voids are disclosed in U.S. Pat. No. 4,968,312 entitled "Disposable Fecal Compartmenting Diaper" issued to Khan on Nov. 6, 1990; U.S. Pat. No. 4,990,147 entitled "Absorbent Article With Elastic Liner For Waste Material Isolation" issued to Freeland on Feb. 5, 1991; U.S. Pat. No. 5,062,840, entitled "Disposable Diapers" issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets" issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition issued Aug. 5, 1997 to Roe, et al. Examples of other structures especially suitable for management of low viscosity feces are disclosed in U.S. Pat. No. 5,941,864 issued to Roe et al. on Aug. 24, 1999; U.S. Pat. No. 5,977,430 issued to Roe et al. on Nov. 2, 1999 and U.S. Pat. No. 6,013,063 issued to Roe et al. on Jan. 11, 2000. All of the above-cited references are hereby incorporated by reference herein.

In addition, the present invention may be suitable for other diaper embodiments including those disclosed in U.S. Pat. No. 6,010,491 titled "Viscous Fluid Bodily Waste Management Article" issued Jan. 4, 2000; U.S. Pat. No. 5,873,870 titled "Fit And Sustained Fit Of A Diaper Via Chassis And Core Modifications" issued Feb. 23, 1999; U.S. Pat. No. 5,897,545 titled "Elastomeric Side Panel for Use with Convertible Absorbent Articles" issued Apr. 27, 1999; U.S. Pat. No. 5,904,673 titled "Absorbent Article With Structural Elastic-Like Film Web Waist Belt" issued May 18, 1999; U.S. Pat. No. 5,931,827 titled "Disposable Pull On Pant" issued Aug. 3, 1999; U.S. Pat. No. 5,977,430 titled "Absorbent Article With Macro-Particulate Storage Structure" issued Nov. 2, 1999 and U.S. Pat. No. 6,004,306 titled "Absorbent Article With Multi-Directional Extensible Side Panels" issued Dec. 21, 1999, the disclosures of which are incorporated herein by reference.

All documents cited are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A unitary disposable absorbent article comprising:
   an absorbent core having a garment surface and a body surface;
   a liquid permeable topsheet positioned adjacent said body surface of said absorbent core;
   a liquid impermeable backsheet positioned adjacent said garment surface of said absorbent care; and
   an elastically contractible dual cuff having a proximate end and a distal end, said dual cuff being joined to said article by an intermediate bond, said dual cuff having a first cuff and a second cuff, said first cuff being disposed between said proximate end and said intermediate bond, said second cuff being disposed between said intermediate bond and said distal end, said dual cuff being constructed of a continuous cuff material and enclosed by a cuff end bond, said cuff end bond being disposed at said distal end and connecting a first edge of the continuous cuff material to a second edge of the continuous cuff material;
   wherein said second cuff is spaced away from said backsheet.

2. The absorbent article of claim 1 wherein said backsheet extends outboard of said distal end.

3. The absorbent article of claim 1 wherein said first cuff envelopes at least one elastic.

4. The absorbent article of claim 3 wherein said elastic is operatively associated with said first cuff by securing it with an elastic attachment element.

5. The absorbent article of claim 1 wherein said second cuff envelopes at least one elastic.

6. The absorbent article of claim 5 wherein said elastic is operatively associated with said second cuff by securing it with an elastic attachment element.

7. The absorbent article of claim 1 wherein said article is a disposable diaper.

8. The absorbent article of claim 7 wherein said disposable diaper is a prefastened diaper.

9. The absorbent article of claim 1 wherein said continuous cuff material is constructed of a lesser-water-permeable material with a more-water-permeable material placed inside said lesser-water-permeable material.

10. The absorbent article of claim 9 wherein said lesser-water-permeable material is a spunbound material.

11. The absorbent article of claim 9 wherein said more-water-permeable material is a meltblown material.

12. The absorbent article of claim 1 wherein said continuous cuff material is constructed of a spunbound-meltblown laminate.

13. The absorbent article of claim 1 wherein said continuous cuff material is constructed of a series of materials.

14. A unitary disposable absorbent article comprising:
    an absorbent core having a garment surface and a body surface;
    a liquid permeable topsbeet positioned adjacent said body surface of said absorbent core;
    a liquid impermeable backsheet positioned adjacent said garment surface of said absorbent core; and
    an elastically contractible dual cuff having a proximate end and a distal end, said dual cuff being joined to said article by an intermediate bond, said dual cuff having a first cuff and a second cuff, said first cuff being disposed between said proximate end and said intermediate bond, said second cuff being disposed between said intermediate bond and said distal end, said dual cuff being constructed of a continuous cuff material and enclosed by a cuff end bond connecting a first edge of the continuous cuff material to a second edge of the continuous cuff material, wherein at least one of said first and second cuffs includes a pair of operatively associated elastic members extending substantially along the length thereof;
    wherein said second cuff is spaced away from said backsheet, wherein said dual cuff is bonded to said article by a single bond.

15. The absorbent article of claim 14 wherein said single bond is said intermediate bond.

16. The absorbent article of claim 1, wherein the first and second cuffs are barrier cuffs.

17. The absorbent article of claim 14, wherein the first and second cuffs each include a pair of operatively associated elastic members.

* * * * *